United States Patent
Sugiyama et al.

[11] Patent Number: 5,543,315
[45] Date of Patent: Aug. 6, 1996

[54] METHOD FOR STABILIZING MEASUREMENT VALUES BY HIGH SPEED LIQUID CHROMATOGRAPHY

[75] Inventors: Koji Sugiyama; Hiroshi Yamamoto, both of Kyoto, Japan

[73] Assignee: Kyoto Daiichi Kagaku Co., Ltd., Kyoto-fu, Japan

[21] Appl. No.: 233,956

[22] Filed: Apr. 28, 1994

Related U.S. Application Data

[63] Continuation-in-part of Ser. No. 82,740, Jun. 8, 1993, abandoned.

[30] Foreign Application Priority Data

Jun. 30, 1992 [JP] Japan ................................ 4-172604

[51] Int. Cl.$^6$ ................................................ G01N 30/02
[52] U.S. Cl. ........................ 436/161; 436/66; 436/67; 436/176; 73/61.52; 73/61.55; 73/61.57; 210/198.2; 210/635; 210/656
[58] Field of Search ............................. 436/66, 67, 161, 436/176; 73/61.52, 61.55, 61.56, 61.57; 210/656, 139, 198.2, 635; 422/70

[56] References Cited

U.S. PATENT DOCUMENTS

| | | | |
|---|---|---|---|
| 4,108,603 | 8/1978 | Regnier et al. | 436/66 |
| 4,142,855 | 3/1979 | Acuff | 422/70 X |
| 4,389,491 | 6/1983 | Hanamoto et al. | 436/67 |
| 4,399,227 | 8/1983 | Niederau et al. | 436/67 |
| 4,407,961 | 10/1983 | Sanders | 436/67 |
| 4,719,017 | 1/1988 | Uchino et al. | 210/656 |
| 4,802,981 | 2/1989 | Kenney et al. | 210/198.2 |
| 4,810,391 | 3/1989 | Bruegger | 210/656 |
| 4,879,039 | 11/1989 | Takahashi et al. | 210/635 |
| 4,969,993 | 11/1990 | Nash Jr. et al. | 210/198.2 |
| 5,039,409 | 8/1991 | Blaffert et al. | 210/198.2 |
| 5,203,992 | 4/1993 | Drouen | 210/198.2 |
| 5,417,853 | 5/1995 | Mizuno et al. | 210/198.2 |

FOREIGN PATENT DOCUMENTS

| | | |
|---|---|---|
| 0316375 | 10/1988 | European Pat. Off. . |
| 0293540 | 12/1988 | European Pat. Off. . |
| 0403680 | 6/1989 | European Pat. Off. . |
| 139683 | 6/1992 | Germany . |

OTHER PUBLICATIONS

Ellis et al. Clinical Chemistry, vol. 30/11, pp. 1746–1752, 1984.
Jeppsson et al. Clinical Chemistry, vol. 32/10, pp. 1867–1872, 1986.
Clin. Chem. 25/11, 1970–1971 (1979).
Clin. Chem. 26/3, 466–472 (1980).
An Instrumental Response . . . Analysis, A Cole, Feb. 1990.

*Primary Examiner*—Jill Warden
*Assistant Examiner*—Maureen M. Wallenhorst
*Attorney, Agent, or Firm*—Birch, Stewart, Kolasch & Birch, LLP.

[57] ABSTRACT

The relationship of variations in the retention time of a specific component of a measurement blood sample with respect to changes in change-over time of the eluting solution is determined. The retention time of the specific component of the measurement blood sample is measured under a particular analyzing condition. In case of a departure of the retention time from a predetermined reference range, a change-over time of eluting solution is obtained in accordance with the relationship, so that the retention time of the specific component can fall within the reference range. The change-ever time of eluting solution is updated as an analyzing condition for the subsequent analysis by using the obtained values.

4 Claims, 6 Drawing Sheets

METHOD FOR STABILIZING MEASUREMENT VALUES BY HIGH SPEED LIQUID CHROMATOGRAPHY

CROSS-REFERENCES TO RELATED APPLICATIONS

This application is a Continuation-in-Part application of the U.S. application Ser. No. 08/082,740 filed on Jun. 28, 1993 now abandoned, the entire contents of which are hereby incorporated by reference.

BACKGROUND OF THE INVENTION

1. Field of the Invention

The present invention relates to a method for stabilizing measurement values in conducting a quantitative analysis of a specific component in a measurement sample by high-speed liquid chromatography.

2. Description of the Prior Art

In the quantitative analysis of a specific component in the measurement sample, for example, glycohemoglobin in a blood sample by the high-speed liquid chromatography, a chromatogram obtained by separating hemoglobin in a separation column is affected by various analyzing conditions and tends to become unstable. For example, the retention time of each component of hemoglobin is varied by the differences in the column, the change with time of the padding material of the column, the temperature of the eluting solution at the time of measurement, the flow rate of the eluting solution, and delicate temperature changes of the column. When the retention time becomes unstable through changes in analyzing parameters, the separation rates of respective components in the chromatogram are varied, resulting in a decrease of measurement accuracy.

Therefore, conventionally in analysis by the high-speed liquid chromatography, the analysis of the measurement sample has been started after first preparing a sample for optimization and optimizing various analyzing parameters such as the adjustments of the concentration of the eluting solutions, change-over time thereof, feed rate thereof, the temperature of the constant temperature bath, and replacement of the column or the like. Furthermore, during the measurement sample analysis, the retention time of a specified component is monitored. Whenever the elution time is over the allowable range, the optimization operation on analyzing parameters as referred to above, has been effected.

However, the conventional optimization operation on the analyzing parameters is completely manual and requires repetitions by trial and error. Therefore, not only is it complicated and time-consuming but also requires a high degree of specialized knowledge and skill in high-speed liquid chromatography. Furthermore, for this reason, there has been such a problem that the analysis of the measurement sample takes a long time.

SUMMARY OF THE INVENTION

The present invention has been developed to solve the problems as referred to above, and an essential object thereof is to provide a stabilizing method for measurement values by high-speed liquid chromatography which is capable of stabilizing measurement values and shortening the analyzing operation on the measurement sample through automatically effecting the optimization of the analyzing parameters.

In order to stabilize the measurement values of the quantity of hemoglobin in the blood, the retention time of at least one eluted component should not be unstable but should be stable in each sample.

According to the present invention, a method for stabilizing measurement values by high-speed liquid chromatography in which a measurement blood sample is transported to a separation column together with eluting solutions and the quantity of each component of said measurement blood sample eluted from said separation column is measured, said stabilizing method comprising the following steps of:

determining the relationship of variations in the retention time of a specific component of a measurement blood sample with respect to changes in change-over time of the eluting solution;

measuring the retention time of said specific component of the measurement blood sample under a particular analyzing parameter;

in case of a departure of said retention time from a predetermined reference range, obtaining a change-over time of eluting solutions in accordance with said relationship, so that said change-over time of eluting solution causes said retention time to fall within the reference range; and updating the change-over time of eluting solution as an analyzing parameter for the subsequent analysis by using said obtained values.

When said updated change-over time does not fall within an allowable range, it may be arranged to inform the operator of an abnormality.

Preferably, retention times of two eluted components should be stable. That is, a relative relation $(t_c-t_a)/(t_0-t_a)$, as shown in FIG. 6, between a retention time of any one of the first eluted components (Hb $A_{1a}$, $A_{1b}$, F, and $A_{1c}$), for example, $t_c$ of Hb $A_{1c}$ and an retention time $A_0$ of last eluted component (Hb $A_0$) should be a constant value, $\alpha_0$.

The inventors discovered the fact that the retention time of each component (Hb $A_{1a}$, $A_{1b}$, F, $A_{1c}$, and $A_0$) of hemoglobin varies according to the changes in the flow rate of eluting solution and that the retention time of the first eluted components (Hb $A_{1a}$, $A_{1b}$, F, and $A_{1c}$) varies according to the changes in the change-over time of eluting solutions and the temperature of eluting solution and separation column.

Suppose that the retention time $t_c'$ of Hb $A_{1c}$ and the retention time $t_0'$ of Hb $A_0$ deviate from the proper values $t_c$, $t_0$ in a chromatogram shown in FIG. 7. In this case, even if the flow rate of eluting solution is changed to bring $t_0'$ of Hb $A_0$ close to $t_0$, the retention time $t_c''$ of Hb $A_{1c}$ which slightly moves toward $t_c$ still deviates from $t_c$ as shown in FIG. 8. As the relation $(t_c''-t_a)/(t_0-t_a)$ in this chromatogram is smaller than the constant value $\alpha_0$, it is not enough to make the measurement value stable. Then the change-over time of eluting solutions or the temperature of eluting solution or separation column is changed to bring $t_c'$ of Hb $A_{1c}$ close to $t_c$, whereby the stable chromatogram as shown in FIG. 6 is obtained.

According to the present invention, a method for stabilizing measurement values by high-speed liquid chromatography in which a measurement blood sample is transported to a separation column together with an eluting solution and the quantity of each hemoglobin component of said measurement blood sample eluted from said separation column is measured, said stabilizing method comprising the following steps of:

determining the first relationship of variations in the retention time of each eluted hemoglobin component with respect to changes in flow rates of eluting solutions and the second relationship of variations in the retention time of each eluted component with respect to changes in at least any one of change-over time of eluting solutions, or temperature of eluting solution or separation column;

measuring the retention time ($t_0$) of hemoglobin $A_0$ in the components of the measurement blood sample under a particular analyzing parameter;

in case of a departure of said retention time ($t_0$) from a predetermined reference range, obtaining a predicted flow rate (Q) of eluting solution in accordance with said first relationship so that said retention time ($t_0$) can be within the reference range;

predicting the retention time ($t_c$) of any one of the first eluted components under the flow rate (Q) of eluting solution in accordance with said first relationship;

in case of a departure of said retention time ($t_c$) from the predetermined reference range, obtaining at least any one of the change-over time ($t_2$) of eluting solution, or the temperature ($T_e$, $T_c$) of eluting solution or separation column in accordance with said second relationship so that said retention time ($t_c$) can fall within the predetermined reference range; and updating the flow rate (Q) of the eluting solution, and at least any one of the change-over time of eluting solutions, the temperature of eluting solution or separation column as analyzing parameters for the subsequent analysis by using said obtained values (Q, and $t_2$, $T_e$ or $T_c$).

In the above step of predicting a retention time ($t_c$) the retention time of hemoglobin $A_{1c}$ in the first eluted components under the flow rate (Q) of eluting solutions may be predicted in accordance with said first relationship.

When said updated flow rate (Q) of eluting solution, or at least any one of said updated change-over time ($t_2$) of eluting solution, or said updated temperature ($T_e$, $T_c$) of eluting solutions or separation column does not fall within an allowable range, notification of an abnormality may be made.

BRIEF DESCRIPTION OF THE DRAWINGS

These and other objects and features of the present invention will become clear from the following description taken in conjunction with the preferred embodiments thereof with reference to the accompanying drawings in which.

DETAILED DESCRIPTION OF THE PREFERRED EMBODIMENTS

Figure 1:
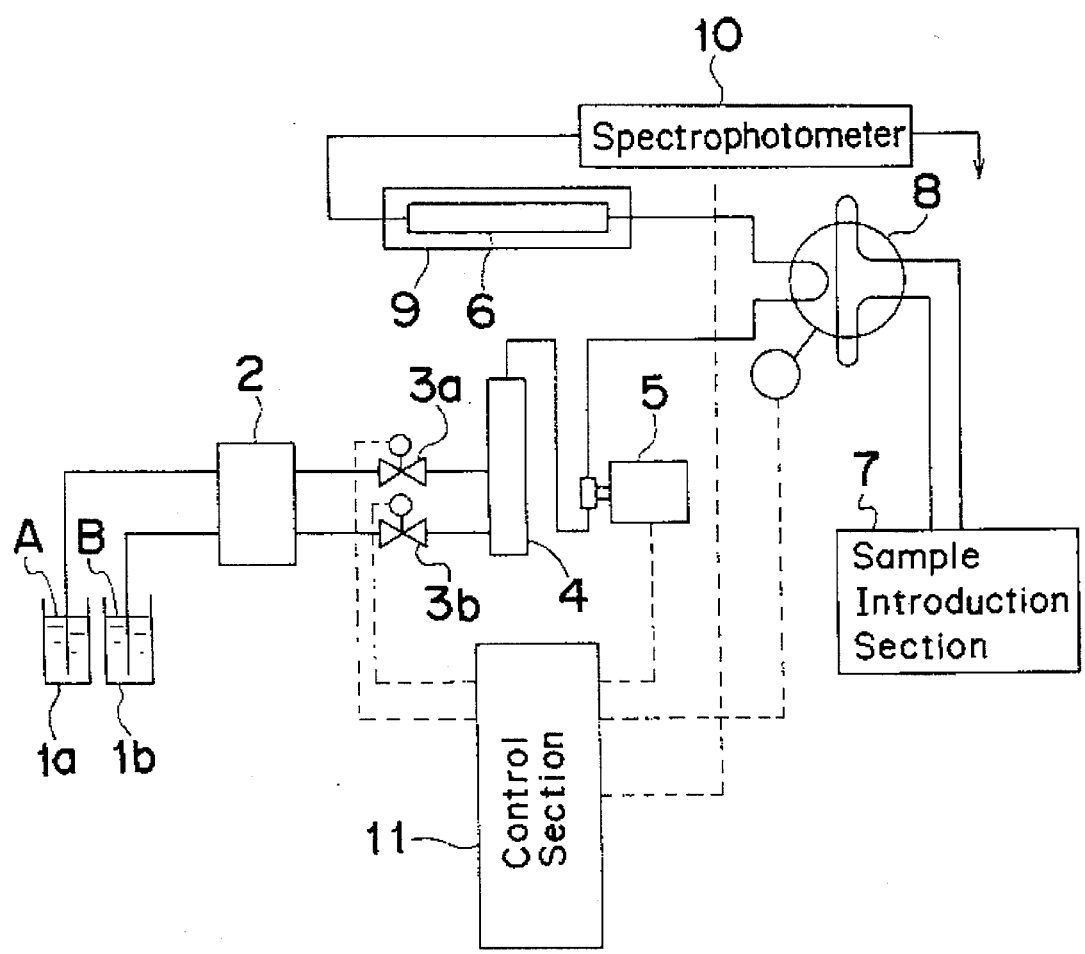
FIG. 1 is a schematic diagram showing an analyzing apparatus the high-speed liquid chromatography wherein the method according to the present invention is carried out.

FIG. 1 is an analyzing apparatus for carrying out the method according to the present invention, in which the quantitative analysis of hemoglobin $A_{1c}$ in the blood (hereinafter referred to merely as Hb $A_{1c}$) by high-speed liquid chromatography method is carried out.

This analyzing apparatus is constituted by a liquid delivery pump 5 for feeding eluting solutions in eluting solution liquid bottles 1a and 1b by sucking through a degas device 2, eluting solution change-over valves 3a, 3b, and a manifold 4, a separation column 6 arranged on the downstream side of the liquid delivery pump 5, a sample injection valve 8 arranged between the separation column 6 and liquid delivery pump 5 to inject a measurement sample (blood) from a sample introduction section 7 into the feed circuit, a constant temperature bath 6 enclosing the separation column 9, a spectrophotometer 10 arranged on the downstream side of the separation column 6 and a control section 11 for controlling the apparatus.

In the eluting solution bottles 1a, 1b, eluting solutions A and B are respectively held. The eluting solutions A and B are phosphate buffers of different concentrations. The elution capacity of eluting solution B with respect to Hb $A_{1c}$ is larger than that of eluting solution A.

The eluting solution change-over valves 3a, 3b are controlled by the control section 11 so that either of them is always opened so as to feed either of the eluting solutions to the separation column 6. The manifold 4 gathers two liquid feeding pipes from eluting solution bottles 1a, 1b for connection to the liquid delivery pump 5.

The liquid delivery pump 5 is a pump of plunger type and feeds the eluting solutions to the separation column 6 under a predetermined pressure of 30 to 200 kg/cm² range.

The sample injection valve 8 is a so-called 6-way valve and injects the sample (blood) introduced from the sample introduction section 7 into the eluting solution feeding circuit.

For the separation column 6, an ion exchange column or a reversed phase distribution column is employed.

The constant temperature bath 9 maintains the temperature of the separation column 6 at a constant value. The spectrophotometer 10 measures the extinction degrees of respective components eluting through the separation column 6 with a measurement wavelength of 415 nm.

The control section 11 controls and operates each portion of the apparatus with a micro computer incorporated therein, and effects the optimization of the analyzing parameters. In the exclusive read-out memory of the control section, there is in advance stored a chart showing the relationship of the variation amount in the retention time of Hb $A_{1c}$ with respect to the changes in the analyzing parameters. In the present embodiment, said analyzing condition is the change-over time $t_2$ (refer to FIG. 3) of switching the eluting solution change-over valve 3b to the eluting solution change-over valve 3a.

The operation of the analyzing apparatus constituted as referred to above will be described below in accordance with the flow chart shown in FIG. 2.

When the power source of the apparatus is put on and the start switch (not Shown) is depressed, the control section 11 first reads out, in Step 101, the analyzing conditions (previous conditions) stored in the rewritable memory. These analyzing conditions are the change-over time of eluting solutions, the temperature of the column constant temperature bath, the flow rate of the liquid feeding pump, and so on. In the next Step 102, the analyzing operation is started by operating each portion under the read-out analyzing conditions.

More specifically, the control section 11 first opens the eluting solution change-over valve 3a and drives the liquid delivery pump 5, whereby the eluting solution A in the eluting solution bottle 1a is fed to the separation column 6 so that the eluting solution passes through the packing material therein. It is to be noted here that the eluting solution A is degassed by the degas device 2 before entering the separation column 6. After the packing material in the separation column 6 comes to the equilibrium, the control section 11 drives the sample injection valve 8 to inject the sample (blood) into the eluting solution A moving in the liquid feeding pipe. Thereby, the sample is transported to the separation column 6 together with the eluting solution A and separated while passing through the packing material so as to be eluted from the separation column in the order of $A_{1a}$, $A_{1b}$, F, and $A_{1c}$.

At a time point $t_1$ after elapse of a predetermined time from injecting the sample (time point $t_s$), the control section 11 closes the eluting solution change-over valve 3a and opens the eluting solution change-over valve 3b to feed the eluting solution B to the separation column 6. Thereby hemoglobin $A_0$ which is the remaining component of the sample is eluted. Subsequently, at a time point $t_2$ after elapse of a predetermined time, the control section 11 closes the eluting solution change-over valve 3b and open the eluting solution change-over valve 3a to feed the eluting solution A to the separation column 6 for effecting equilibration thereof.

Figure 3:
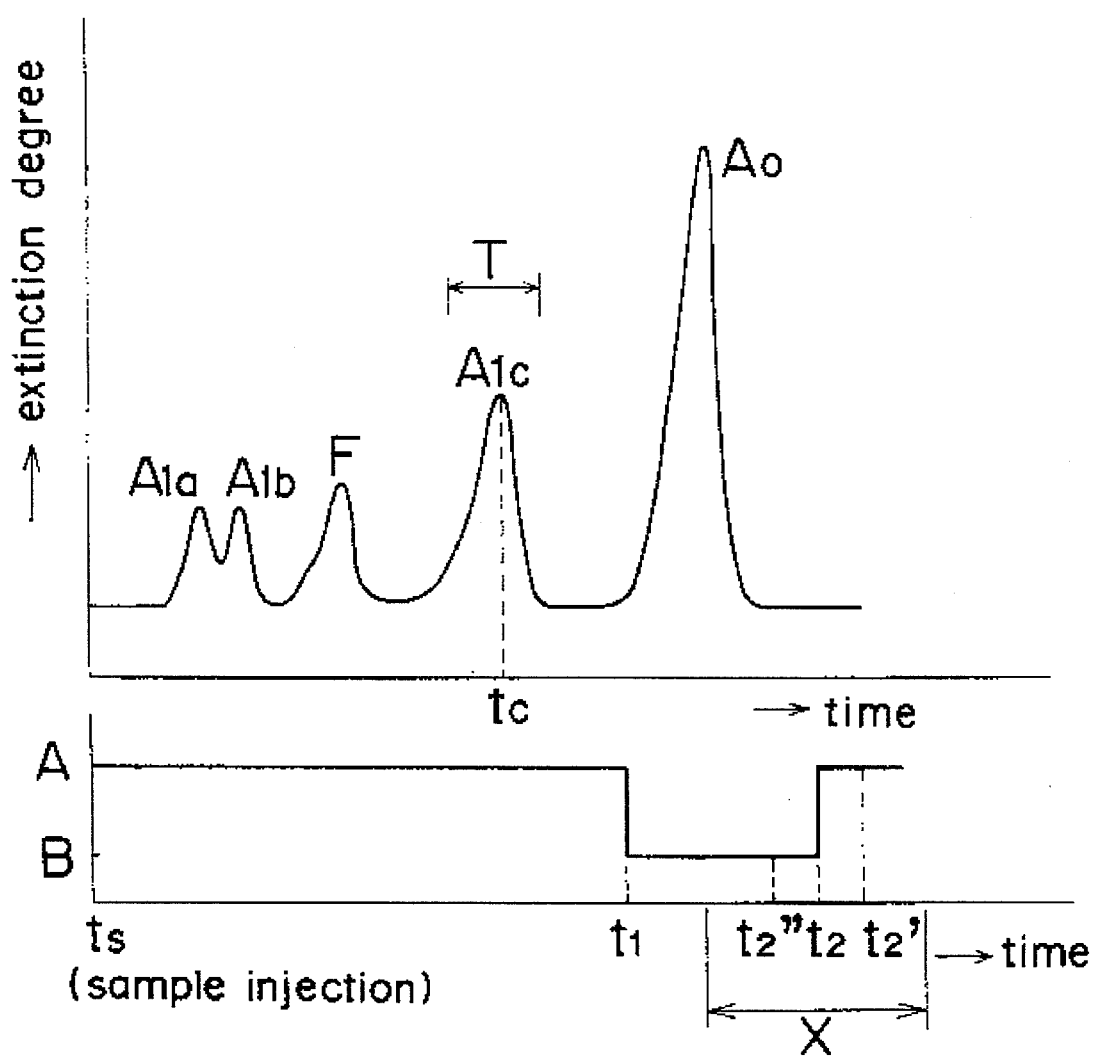
FIG. 3 is a chromatogram of hemoglobin and a time chart for change-over of the eluting solution.

Respective components of the sample eluting through separation in the separation column 6 are measured by the spectrometer 10 in respect of the extinction degree thereof and a chromatogram as shown in FIG. 3 is obtained.

After the analyzing operation as described above, the control section 11 memorizes, at Step 103, the chromatogram in the memory, and identifies, at Step 104, Hb $A_{1c}$. The identification of Hb $A_{1c}$ can be made by finding the fourth peak of the extinction degree after injection (time point $t_s$) of the sample or the second peak from the last. After identifying Hb $A_{1c}$ in this manner, the time from the time-point of the sample injection ($t_s$) to the time point of the peak point of extinction degree is obtained as the retention time of $t_c$ of Hb $A_{1c}$.

In next Step 105, the control section 11 judges whether this retention time $t_c$ falls within the proper range of the chromatogram of hemoglobin, and if it is within the proper range, it proceeds to Step 106 and when the next sample is present, it returns to Step 101 to repeat the analysis of the next sample in the same manner and if not present, it terminates the analysis.

In said Step 105, if the retention time $t_c$ of Hb $A_{1c}$ is not within the proper range, it judges, in Step 107, whether the retention time $t_c$ is advanced or delayed from the proper range. Here, when the retention time $t_c$ of Hb $A_{1c}$ is delayed from the proper range T, the change-over time $t_2$ to the eluting solution A is delayed, in Step 108, to $t_2'$ in accordance with the chart memorized beforehand in the exclusive read-out memory. Since the equilibrium time of the column by the eluting solution A is thereby shortened and the eluting solution B which is easier to elute hemoglobin in the next analysis remains longer in the separation column, the retention time $t_c$ of Hb $A_{1c}$ at the subsequent analysis is advanced so as to fall within the proper range T.

On the contrary, when the retention time $t_c$ of Hb $A_{1c}$ is advanced, the change-over time to $t_2$ the eluting solution A is advanced to $t_1'''$ in Step 109. Thereby, the effect of the eluting solution B in the next analysis is reduced and the retention time $t_c$ of Hb $A_{1c}$ at the next analysis is delayed so as to fall within the proper range.

In next Step 110, the control section 11 judges whether or not the analyzing conditions (eluting solution change-over time) modified in said Step 108 or 109 are within the allowable range. Namely, in the case where the modified eluting solution change-over time $t_2''$ is extremely advanced so as to come close to $t_1'$ or $t_2'$ is very much delayed so as to come close to the next analysis starting time, the packing material in the separation column 6 is considered to be deteriorated and, the judgement of its life is effected here.

When the modified value of said analyzing parameters (eluting solution change-over time) is within the proper range X, after updating the eluting solution change-over time among the analyzing parameters to $t_2'$ or $t_2''$ in Step 111, the operation process returns to Step 101 through 106, while when it is not within the allowable range X, an abnormality is notified in Step 112 with a buzzer, a lamp or the like so as to urge the operator to replace the separation column 6.

In the above-described embodiment, it is arranged to modify the change-over time from eluting solution B to eluting solution A among the analyzing conditions so that the retention time of Hb $A_{1c}$ falls within the proper range. The present invention is not limited to this situation but the modification of the flow rate of the liquid delivery pump 5 or the temperature of the separation column 6 may be applicable. Namely, in the case of the flow rate of the liquid delivery pump 5, when the retention time of Hb $A_{1c}$ is advanced compared with the proper range, the flow rate is reduced and when it is delayed, the flow rate is increased. Meanwhile, in the case of the temperature of the separation column 6, when the retention time of Hb $A_{1c}$ is advanced in comparison with the proper range, the temperature is reduced and when it is delayed, the temperature is increased.

Figure 4:
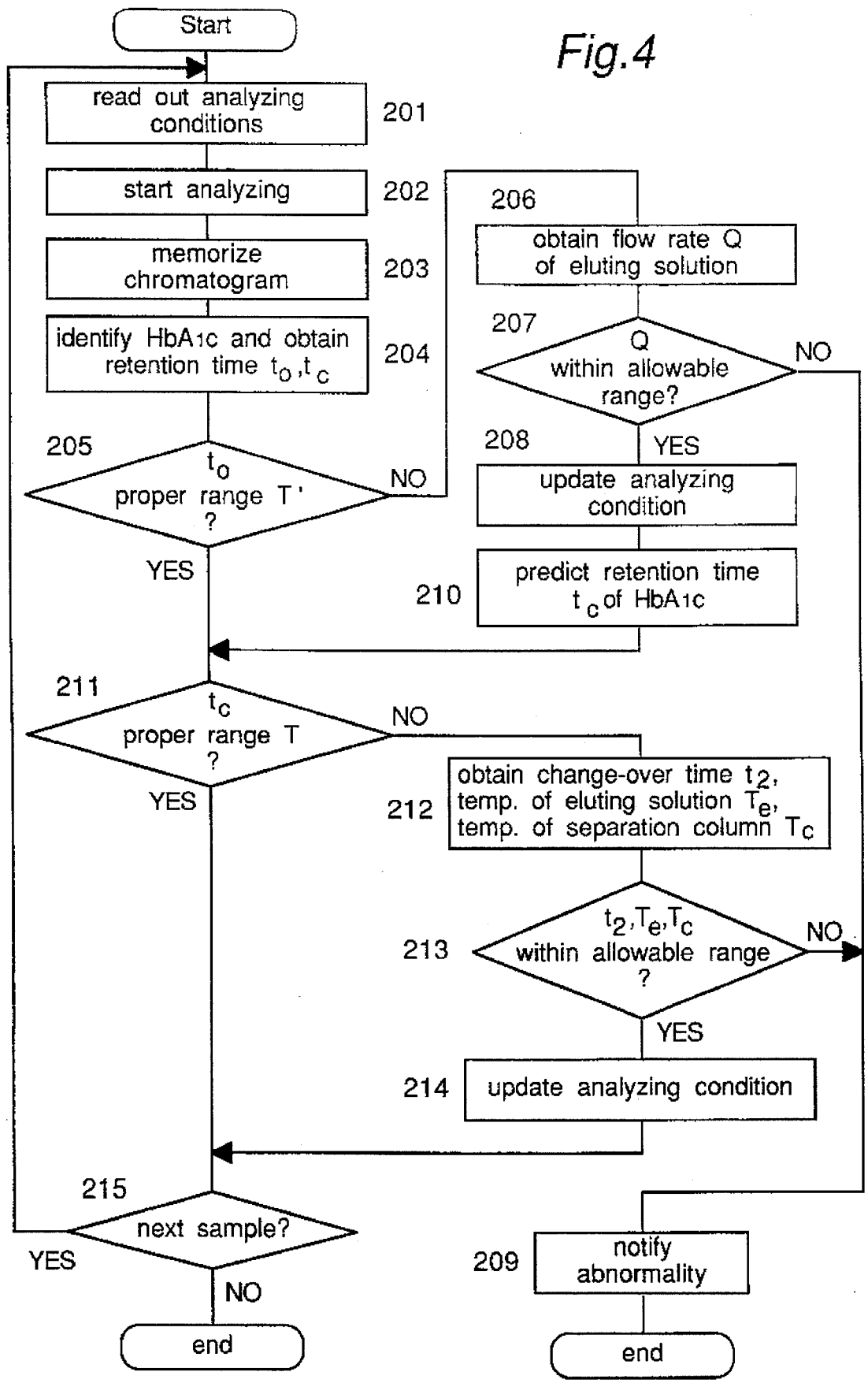
FIG. 4 is a flow chart showing the control operation by a microcomputer according to the another embodiment of the present invention.

FIG. 4 shows another embodiment of the method according to the present invention. This method can be executed by using the same apparatus as that shown in FIG. 1. In the exclusive read-out memory of the control section 11, there are in advance stored some charts showing a first relationship of variations in the retention time of each eluted component (Hb $A_{1a}$, $A_{1b}$, F, $A_{1c}$, $A_0$) with respect to changes in flow rates of eluting solution and a second relationship of variations in the retention time of each eluted component with respect to changes in change-over time of eluting solutions and temperatures of eluting solutions and separation column.

Figure 2:
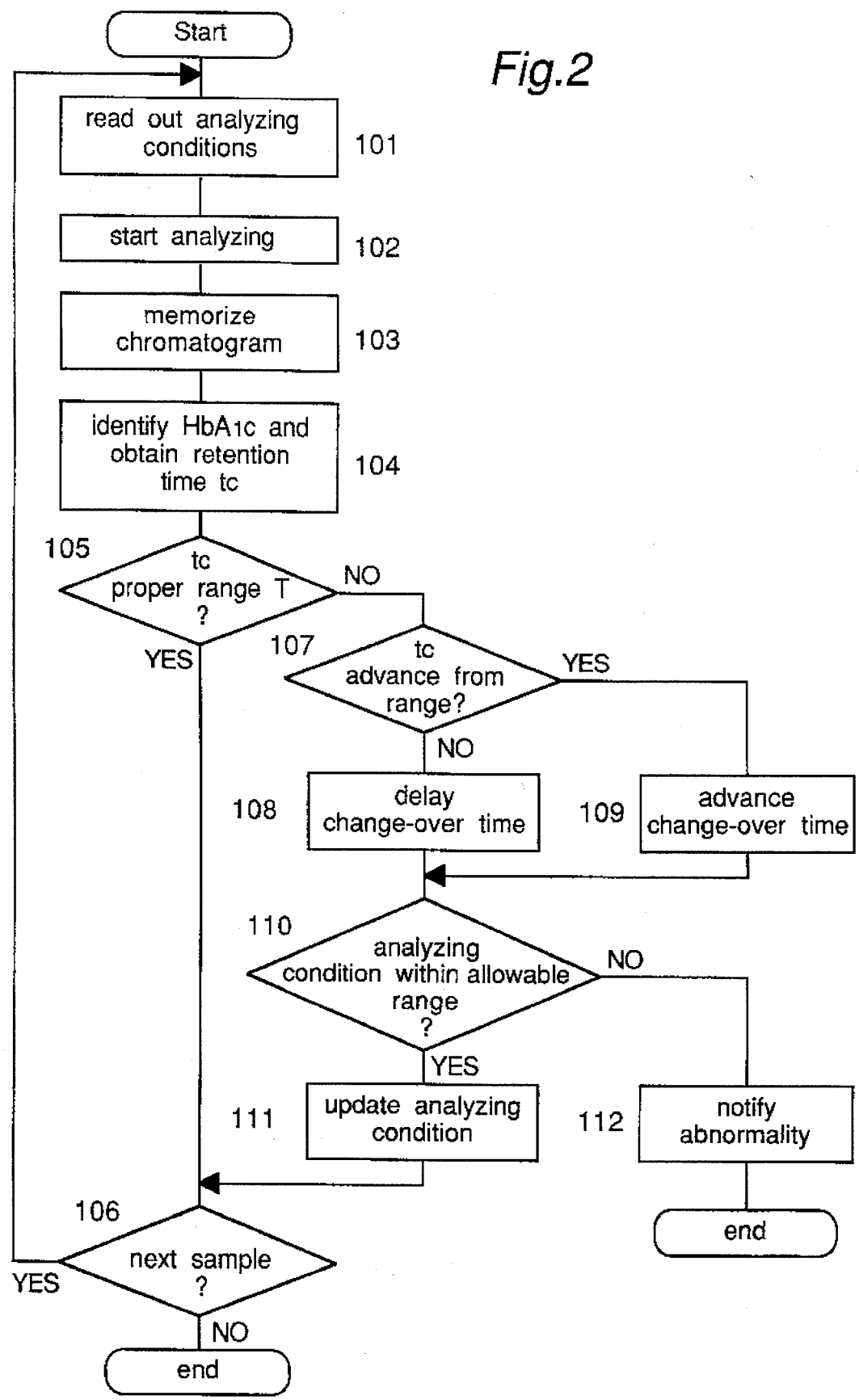
FIG. 2 is a flow chart showing the control operation by a micro computer.

Depressing the start switch causes the control section 11 to start the analysis and execute Step 201 to 204 in the same manner as aforementioned embodiment (FIG. 2). In Step 204, the time at the peak point of Hb $A_{1c}$ is measured as a retention time ($t_c$) of Hb $A_{1c}$ and at the same time the time at the last peak point is measured as a retention time ($t_0$) of Hb $A_0$.

Figure 5:
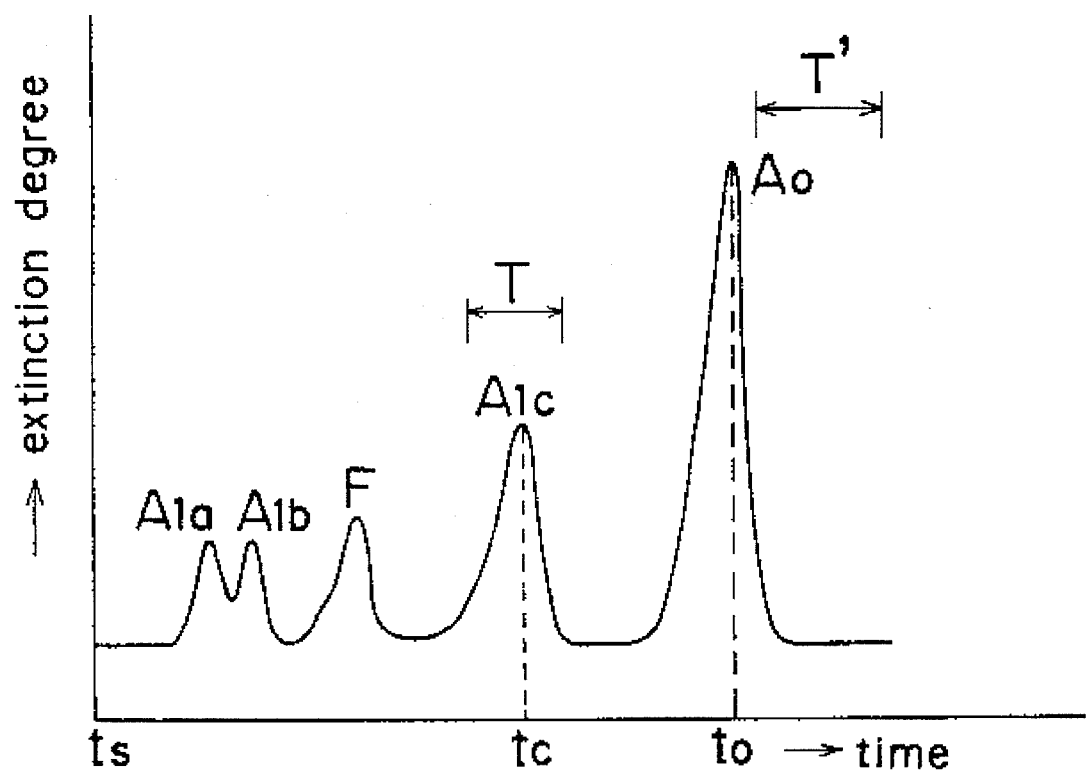
FIG. 5 is an another chromatogram of hemoglobin.
Figure 6:
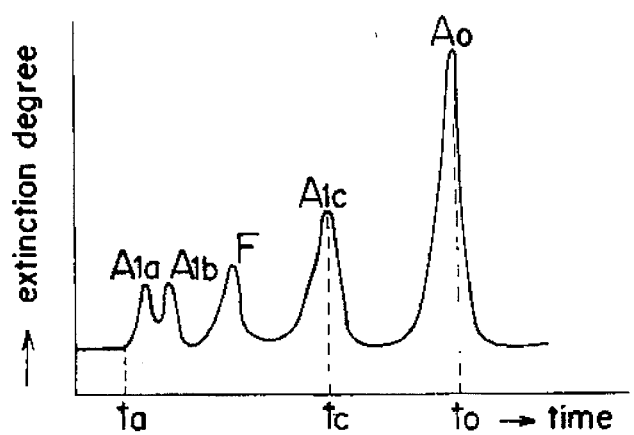
FIG. 6 is an example of stable and acceptable chromatogram of hemoglobin.
Figure 7:
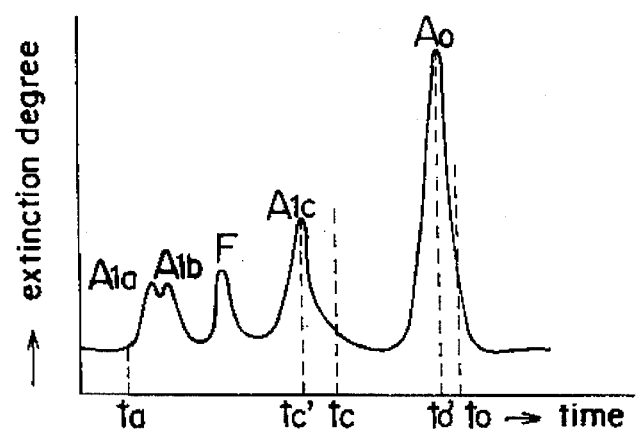
FIG. 7 is an example of unstable chromatogram of hemoglobin.
Figure 8:
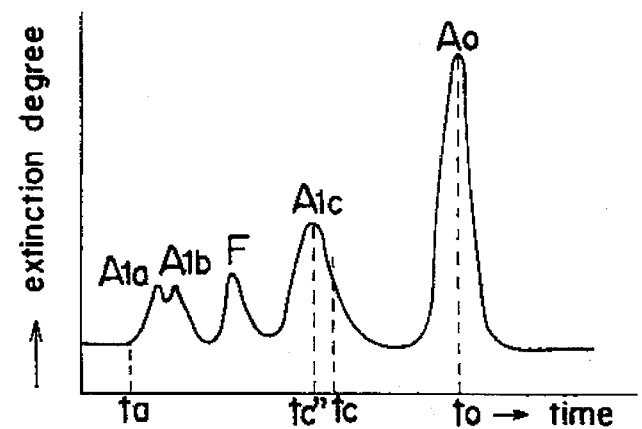
FIG. 8 is an example of unstable chromatogram of hemoglobin obtained by changing the flow rate of eluting solution under the chromatogram shown in FIG. 7.

In next Step 205, the control section 11 judges whether or not the retention time ($t_0$) falls within the proper range T' as shown in FIG. 5. If $t_0$ is within the range T', whether the retention time ($t_c$) falls within the proper range T or not is also judged in Step 211. If $t_c$ is within the range T, analysis of the next sample is commenced after returning to Step 201 through Step 215.

In said Step 205, if the retention time $t_0$ is beyond the range T', a predicted rate Q of eluting solution is obtained in Step 206 in accordance with the first relationship stored in the memory of the control section 11 so that $t_0$ can be within the range T'. Then, whether the predicted flow rate Q obtained in Step 206 is within allowable range or not is decided in Step 207. In case Q is within the range, the control section 11 updates the flow rate of eluting solution in analyzing conditions by using the predicted flow rate Q obtained in Step 208; while in case Q is not within the range, an abnormality is notified in Step 209.

After updating the analyzing condition, the control section 11 predicts, in Step 210, a retention time $t_c$ of Hb $A_{1c}$ under the flow rate Q of the eluting solution obtained in Step 206 in accordance with said first relationship and decides, in Step 211, whether or not the retention time $t_c$ predicted in Step 210 falls within a proper range T as shown in FIG. 5. If it is within the range T, the next sample is analyzed after returning to Step 201 through Step 215; while if it is not within the range T, a change-over time $t_2$ of eluting solution, a temperature $T_e$ of the eluting solution and a temperature $T_c$ of the separation column 6 under the retention time $t_c$ predicted in Step 210 are obtained in Step 212 in accordance with the second relationship stored in the memory of the control section 11. Then, in case that the change-over time $t_2$ and the temperature $T_e$, $T_c$ are within an allowable range as a result of decision in Step 213, the change-over time of eluting solution and the temperatures of eluting solution and separation column 6 in the analyzing conditions are updated by using the change-over time $t_2$ and the temperatures $T_e$, $T_c$ obtained in Step 212; while in case that any one of the change-over $t_2$ or the temperature $T_e$, $T_c$ are not within the range, an abnormality is notified in Step 209. After updating the analyzing parameter in Step 214, the control section 11 repeats the analysis of the next sample under the updated conditions.

In the above embodiment, the retention time $t_o$ of Hb $A_0$ will be within the proper range T' by updating the flow rate of eluting solution. And the retention time $t_c$ of Hb $A_{1c}$ will be also within the proper range by updating the change-over time of eluting solution, and the temperatures of eluting solution and separation column 6. Therefore, the chromatograph of hemoglobin in the blood will be stable, which causes enhancement of the accuracy of measurements.

Although the change-over time of eluting solution and the temperatures of both eluting solution and the separation column are obtained in Step 213 of the above embodiment, any one of the change-over time of eluting solution, or the temperature of eluting solution or separation column may be obtained and updated.

As is clear from the foregoing description, according to a first aspect of the present invention, since the analyzing parameter are modified to the optimum state at all times, the measurement accuracy is improved. Furthermore, since the optimization of the analyzing parameter is automatically effected, the operations for optimizing the analyzing parameter, which is complicated and requires knowledge and skill of a high level, become unnecessary. The time required for the analysis of a measurement sample is shortened, resulting in labor saving.

Furthermore, according to a second aspect of the present invention, when a modified analyzing condition does not fall within the allowable range, it is arranged to notify the operator of an abnormality. Therefore, the operator can readily judge the life of the separation column by said notification before an error takes place in the measurement value, and can promptly take a proper measure such as the replacement of the separation column, etc.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for stabilizing measurement values by high-speed liquid chromatography in which a measurement blood sample is transported to a separation column together with one of two eluting solutions and the quantity of each hemoglobin component of said measurement blood sample eluted from said separation column is measured, said stabilizing method comprising the following steps of:

determining a first relationship of variations in retention times of each eluted hemoglobin component with respect to variations in flow rates of the eluting solutions and a second relationship of variations in retention times of each eluted hemoglobin component with respect to variations in at least any one of change-over time of eluting solutions, temperature of the eluting solutions or temperature of the separation column;

measuring the retention time ($t_0$) of the last eluted, hemoglobin $A_0$ component of the measurement blood sample;

wherein in the case of a departure of said retention time ($t_0$) from a predetermined reference range, obtaining a predicted flow rate (Q) of eluting solutions in accordance with said first relationship so that said retention time ($t_0$) will fall within the reference range;

obtaining a predicted retention time ($t_c$) of any one of the first eluted hemoglobin components, Hb $A_{1a}$, $A_{1b}$, F or $A_{1c}$, in said measurement blood sample, under the predicted flow rate (Q) of eluting solutions in accordance with said first relationship;

wherein in the case of a departure of said predicted retention time ($t_0$) from a predetermined reference range, obtaining at least any one of predicted change-over time ($t_2$) of eluting solutions or a predicted temperature ($T_e$) of eluting solutions or a predicted temperature ($T_c$) of the separation column in accordance with said second relationship so that said predicted retention time ($t_c$) will fall within the reference range; and updating the flow rate of eluting solutions and at least any one of the change-over time of eluting solutions, the temperature of eluting solutions or the temperature of the separation column, as analyzing parameters for subsequent analysis by using said obtained predicted values (Q, and $t_2$, or $T_e$ or $T_c$).

2. The method for stabilizing measurement values by high-speed liquid chromatography as claimed in claim 1, wherein in the step of obtaining a predicted retention time ($t_0$), the retention time of hemoglobin $A_{1c}$ under said predicted flow rate (Q) of eluting solutions is predicted in accordance with said first relationship.

3. The method for stabilizing measurement values by high-speed liquid chromatography as claimed in claim 1, wherein when said predicted flow rate (Q) of eluting solutions does not fall within an allowable range, notification of an abnormality is made.

4. The method for stabilizing measurement values by high-speed liquid chromatography as claimed in claim 1, wherein when at least any one of said predicted change-over time ($t_2$) of eluting solutions, or said predicted temperatures ($T_e$, $T_c$) of eluting solutions or separation column does not fall within an allowable range, notification of an abnormality is made.

* * * * *